(12) United States Patent
Cho et al.

(10) Patent No.: US 6,768,019 B2
(45) Date of Patent: Jul. 27, 2004

(54) 3,4-DIHYDRO-1H-NAPHTHALENE DERIVATIVES AS A HIGHLY SELECTIVE CYCLOOXYGENASE-2 INHIBITOR

(75) Inventors: Ii Hwan Cho, Seoul (KR); Jee Woong Lim, Gyeonggi-do (KR); Ji Young Noh, Busan (KR); Jong Hoon Kim, Gyeonggi-do (KR); Sang Wook Park, Gyeonggi-do (KR); Hyung Chul Ryu, Gyeonggi-do (KR); Je Hak Kim, Gyeonggi-do (KR); Hyung Ok Chun, Gyeonggi-do (KR); So Young Wang, Seoul (KR); Sung Hak Lee, Seoul (KR)

(73) Assignee: Cheil Jedang Corporation, Seoul (KR)

( * ) Notice: Subject to any disclaimer, the term of this patent is extended or adjusted under 35 U.S.C. 154(b) by 0 days.

(21) Appl. No.: 10/456,065

(22) Filed: Jun. 5, 2003

(65) Prior Publication Data
US 2003/0187302 A1 Oct. 2, 2003

Related U.S. Application Data

(62) Division of application No. 10/264,073, filed on Oct. 3, 2002, now Pat. No. 6,686,493.

(30) Foreign Application Priority Data

Oct. 10, 2001 (KR) ........................................ 2001-62488

(51) Int. Cl.$^7$ ............................................. C07C 251/32
(52) U.S. Cl. ......................... 558/61; 558/410; 564/265
(58) Field of Search ................... 558/61, 410; 564/265

(56) References Cited

FOREIGN PATENT DOCUMENTS

WO    WO 95/00501    1/1995

*Primary Examiner*—Ceila Chang
*Assistant Examiner*—Golam M M Shameem
(74) *Attorney, Agent, or Firm*—Swanson &Bratschun, L.L.C.

(57) ABSTRACT

The present invention relates to a novel 3,4-dihydro-1H-naphthalene derivative having a structure of formula 1 or formula 2, its pharmaceutically acceptable salts and their geometric isomers as a highly selective cyclooxygenase-2 inhibitor.

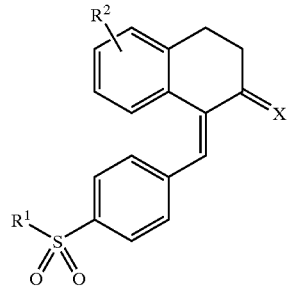

<Formula 1>

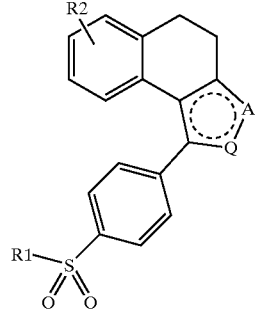

<Formula 2>

Wherein $R^1$, $R^2$, X, A and Q are defined in this specification respectively.

4 Claims, No Drawings

3,4-DIHYDRO-1H-NAPHTHALENE DERIVATIVES AS A HIGHLY SELECTIVE CYCLOOXYGENASE-2 INHIBITOR

RELATED APPLICATIONS

This application is a divisional application of U.S. patent application Ser. No. 10/264,073, filed Oct. 3, 2002, now U.S. Pat. No. 6,686,493 entitled 3,4-Dihydro-1H-naphthalene derivatives as a highly selective cyclooxygenase-2 inhibitor which claims priority to Korean patent application no. 2001-62488,filed Oct. 10, 2001 entitled 3,4-Dihydro-1H-naphthalene derivatives as a highly selective cyclooxygenase-2 inhibitor which is incorporated herein by reference in its entirety.

TECHNICAL FIELD

The present invention relates to 3,4-dihydro-1H-naphthalene derivatives as a highly selective cyclooxygenase-2 inhibitor.

BACKGROUND

Most of non-steroid anti-inflammatory drugs represent actions such as anti-inflammation, ataralgesia, defervescence by inhibiting the enzymatic activity of cyclooxygenase or prostaglandin G/H synthase. In addition, they can suppress the uterine contraction induced by hormones and the cell proliferation in several kinds of cancers. First, only cyclooxygenase-1 was known to be found in cow as a constitutional enzyme. But, recently, cyclooxygenase-2 is elucidated as an induced form. Cyclooxygenase-2 is identified to be discriminated clearly from cyclooxygenase-1 and can be provoked easily by mitogen, endotoxin, hormones, growth factors, cytokines and the like.

Prostaglandins have various pathological and physiological functions. Precisely, cyclooxygenase-1 as a constitutional enzyme participates in the secretion of basic endogenous prostaglandin and plays an important role in physiological aspects such as stomach homeostasis, renal blood circulation and so on. On the other hand, cyclooxygenase-2 is induced by inflammatory factors, hormones, growth factors, cytokines and the like and thus plays an important role in pathological effects of prostaglandins. Therefore, selective inhibitors against cyclooxygenase-2 are expected to have no side effect on account of the functional mechanism compared with the anti-inflammatory drugs such as conventional non-steroid agents and to represent actions such as anti-inflammation, ataralgesia and defervescence. Furthermore, it is estimated to suppress the uterine contraction induced by hormones and the cell proliferation in several kinds of cancers. Especially, it probably has lesser side effects such as gastrointestinal toxicity, renal toxicity and the like. Also, it is assumed to prevent the synthesis of contractive prostanoids and thus inhibit the contraction of smooth muscle induced by the prostanoid. Hence, it can be applied usefully to treat a premature birth, dysmenorrhea, asthma and several diseases associated with eosinophilic leukocytes. Besides, it can be exploited widely to cure osteoporosis, glaucoma and athymia, which has been disclosed in a lot of references, especially the usefulness of selective inhibitors against cyclooxygenase-2 (References: John Vane, "Towards a better aspirin" in *Nature*, Vol. 367, pp 215–216, 1994; Bruno Battistini, Regina Botting and Y. S. Bakhle, "COX-1 and COX-2; Toward the Development of More Selective NSAIDs" in *Drug News and Perspectives*, Vol. 7, pp 501–512, 1994; David B. Reitz and Karen Seibert, "Selective Cyclooxygenase Inhibitors" in *Annual Reports in Medicinal Chemistry*, James A. Bristol, Editor, Vol. 30, pp 179–188, 1995).

The selective inhibitors against cyclooxygenase-2 have been reported to have various structural forms. Among these, the diaryl heterocycle structure, namely a tricyclic system, has been studied most frequently and exploited to construct a lot of candidate substances. In this structure, it is essential that sulfonamide or methanesulfone group exist onto one phenyl group. The initial substance of such a structure is identified to be Dup697 (Bioorganic and Medicinal Chemistry Letters, Vol. 5, No. 18, p 2123, 1995). Then, as a derivative, SC-58635 (Journal of Medicinal Chemistry, Vol. 40, p 1347, 1997) having a pyrrazole structure, MK-966 (WO 95/00501) having a furanone structure and the like are disclosed.

DISCLOSURE OF INVENTION

Based upon the above technical backgrounds, the inventors of the present invention have tried a lot in order to develop novel compounds as a highly selective cyclooxygenase-2 inhibitor. As a result, we have found that 3,4-dihydro-1H-naphthalene derivatives of formula 1 and formula 2 satisfied such a purpose and completed the present invention successfully. It was identified that the compounds of the present invention contain sulfoneamidophenyl or methanesulfonylphenyl group as a specific structure of conventional chemicals and namely, is based upon a structure fused in between two or three rings which is very different from typical tricycle structures.

Therefore, the object of the present invention is to provide 3,4-dihydro-1H-naphthalene derivatives of formula 1 and formula 2 as depicted below.

Hereinafter, the present invention will be described more clearly.

The present invention relates to 3,4-dihydro-1H-naphthalene derivatives of formula 1 and formula 2.

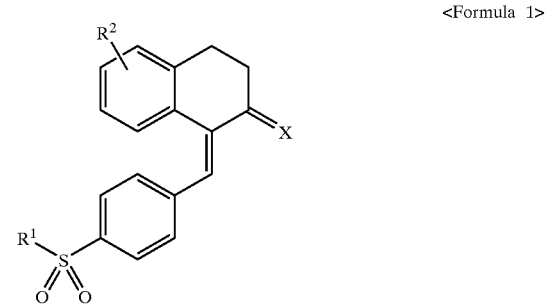

<Formula 1>

<Formula 2>

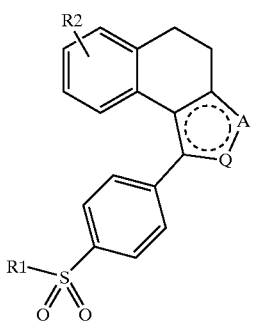

Wherein, R¹ is methyl or amino group,

R² is hydrogen, halogen (fluoride, chloride, bromide and so on), $C_1$-$C_3$-alkyl (methyl, ethyl and so on) substituted or not substituted by halogens, amino, hydroxy, hydoxycarbonyl, nitro or cyano group, X is oxygen (═O), sulfur (═S) or oxime (═N—OH) as a substituted or not substituted form in which a substituent of said oxime can be $C_1$-$C_3$-alkyl substituted or not substituted by halogens; $C_3$-$C_7$-cycloalkyl; $C_1$-$C_5$-alkyl containing 1~3 ether bonds and/or an aryl substituent; substituted or not substituted phenyl; substituted or not substituted five or six ring-cycled heteroaryl containing more than one hetero atoms selected from a group consisting of nitrogen, sulfur and oxygen (wherein, phenyl or heteroaryl can be one- or multi-substituted by a substituent selected from a group consisting of hydrogen, methyl, ethyl and isopropyl); $C_1$-$C_3$-alkylcarbonyl; halogeno-$C_1$-$C_3$-alkylcarbonyl; $C_3$-$C_7$-cycloalkylcarbonyl; or $C_1$-$C_5$-alkylcarbonyl containing 1~3 ether bonds (—O—) and/or aryl substituent, A and Q can be a nitrogen or oxygen atom independently, in which said nitrogen atom can be substituted by a substituent selected from a group consisting of hydrogen, methyl, ethyl and isopropyl.

The compound of the present invention can be a geometric isomer of a cis or a trans form and a mixture of these isomers, depending upon a substituent arranged around double bonds. Consequently, the geometric isomer or the mixture also can be within the scope and limit of the present invention.

The compound of the present invention can exist as a pharmaceutically acceptable salt form, wherein the pharmaceutically acceptable salt means a nontoxic salt containing organic salt and inorganic salt and accepted pharmaceutically. The inorganic salt consists of aluminum, ammonium, calcium, copper, iron, lithium, magnesium, manganese, potassium, sodium, zinc and the like and preferably, ammonium, calcium, magnesium, potassium, sodium. The organic salt consists of primary-, secondary- or tertiary-amines, naturally substituted amines, cyclic amines, modified salts prepared through basic ion exchange resin and the like. Preferably, the organic salt can be selected among arginine, betain, caffeine, colin, N,N-dibenzylethylenediamine, diethylamine, 2-diethylaminoethanol, 2-dimethylaminoethanol, ethanolamine, ethylenediamine, N-ethylmorpholine, N-ethylpiperidine, N-methylglucamine, glucamine, glucosamine, histidine, hydrapamine, N-(2-hydroxyethyl) piperidine, N-(2-hydroxyethyl)pyrrolidine, isopropylamine, lysine, methylglucamine, morpholine, piperazine, piperidine, polyamine resin, procain, purine, teobromine, triethylamine, trimethylamine, tripropylamine, tromethamine and the like.

Besides, the compound of the present invention can be a salt form of nontoxic acids containing the organic acid and the inorganic acid and accepted pharmaceutically, in case that it be basic. Preferably, the acid can be adopted among acetic acid, adipic acid, aspartic acid, 1,5-naphthalenedisulfonic acid, benzenesufonic acid, benzo acid, camposulfonic acid, citric acid, 1,2-ethanedisulfonic acid, ethanesulfonic acid, ethylendiaminetetraacetic acid, fumaric acid, glucoheptonic acid, gluconic acid, glutamic acid, hydriodic acid, hydrobromic acid, hydrochloric acid, icethionic acid, lactic acid, maleic acid, malic acid, manderic acid, methanesulfonic acid, music acid, 2-naphthalene disulfonic acid, nitric acid, oxalic acid, parnoic acid, pantothenic acid, phosphoric acid, pivalic acid, propionic acid, salicylic acid, stearic acid, succinic acid, sulfuric acid, tartaric acid, p-toluenesulfonic acid, undecanoic acid, 10-undecenoic acid and the like and more preferably, among succinic acid, hydrobromic acid, hydrochloric acid, maleic acid, methanesulfonic acid, phosphoric acid, sulfuric acid, tartaric acid and the like.

Preferably, the compound of the present invention of formula 1 as a selective inhibitor against cyclooxygenase-2 is that R¹ is methyl, R² is hydrogen, X is oxygen (═O) or sulfur (═S) or oxime (═N—OH) substituted or not substituted, in which the substituent of the oxime can be selected among methyl, ethyl, benzyl, acetyl or benzyloxy-acetyl compounds. In addition, the present compound of formula 2 is preferable that R¹ is methyl, R² is hydrogen, A is nitrogen, Q is oxygen or nitrogen substituted or not substituted by methyl.

For preferred embodiments of the present invention, the compounds of formula 1 will be described more clearly as follows:

(E)-1-(4-methanesulfonyl-benzylidene)-3,4-dihydro-1H-naphthalene-2-one;

(E)-1-(4-methanesulfonyl-benzylidene)-3,4-dihydro-1H-naphthalene-2-one oxime;

(E)-1-(4-methanesulfonyl-benzylidene)-3,4-dihydro-1H-naphthalene-2-one O-ethyl-oxime;

(E)-1-(4-methanesulfonyl-benzylidene)-3,4-dihydro-1H-naphthalene-2-one O-methyl-oxime;

(E)-1-(4-methanesulfonyl-benzylidene)-3,4-dihydro-1H-naphthalene-2-one O-benzyl-oxime;

1-(4-methanesulfonyl-phenyl)-4,5-dihydro-2H-benzo[e]indazole;

1-(4-methanesulfonyl-phenyl)-4,5-dihydro-naphtho[2,1-c]isooxazole;

(E)-1-(4-methanesulfonyl-benzylidene)-3,4-dihydro-1H-naphthalene-2-one O-acetyl-oxime;

(E)-1-(4-methanesulfonyl-benzylidene)-3,4-dihydro-1H-naphthalene-2-one O-(benzyloxyacetyl)-oxime; and 1-(4-methanesulfonyl-phenyl)-2-methyl-4,5-dihydro-2H-benzo[e]imidazole.

On the other hand, the compounds of formula 1 or formula 2 in the present invention can be prepared by performing the procedures as illustrated below.

However, the process for preparing the compounds of the present invention will not be restricted to following descriptions, especially in reaction solvents, bases, amounts of used reactants and the like.

Moreover, the compound of the present invention also can be prepared by exploiting and combining various synthetic methods described in the present specification or disclosed in other references of those skilled in this arts with a coordinate and arbitrary mode.

Those skilled in the art will appreciate that the conceptions and specific embodiments disclosed in the foregoing description may be readily utilized as a basis for modifying or designing other embodiments.

Concretely, the compound of formula 1 in the present invention can be prepared by the processes as follows:

(a) producing the compound of formula 1a, in which a benzaldehyde derivative of formula 3 is reacted with a beta-tetralone derivative of formula 4 under the presence of a solvent with an acid catalyst; or (b) producing the compound of formula 1b, in which the compound of formula 1a is reacted with hydroxylamine under the presence of a solvent with an arbitrary base; or (c) producing the compound of formula 1c, in which the compound of formula 1b is reacted with a halogen compound of formula 5 under the presence of an organic base by performing a nucleophilic substitution; or (d) producing the compound of formula 2, in which the compound of formula 1aa is reacted with a non-substituted hydrazine, $C_1$–$C_3$-alkyl-substituted hydrazine or hydroxylamine under the presence of solvent by performing ring-closure.

<Formula 3>

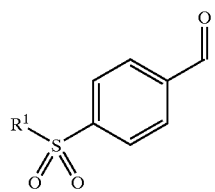

<Formula 4>

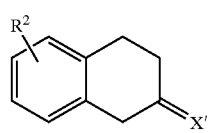

<Formula 1a>

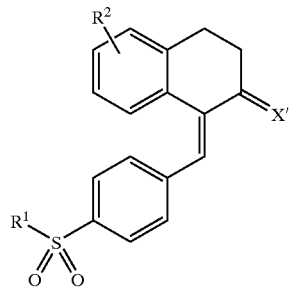

<Formula 1b>

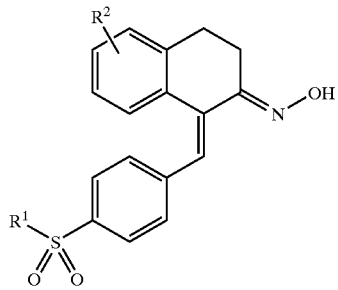

<Formula 5>

R—Hal

<Formula 1c>

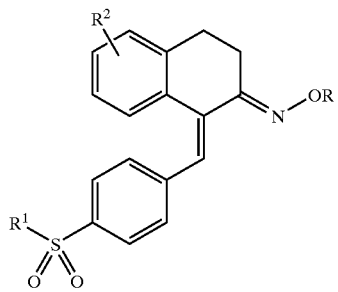

<Formula 1aa>

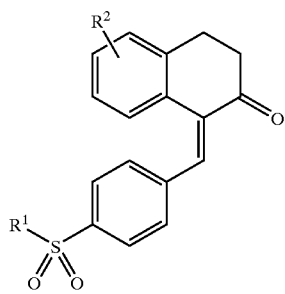

Wherein, $R^1$ and $R^2$ are defined above,

X' is oxygen or sulfur,

R is $C_1$–$C_3$-alkyl substituted or not substituted by halogens; $C_3$–$C_7$-cycloalkyl; $C_1$–$C_5$-alkyl containing 1~3 ether bonds (—O—) and/or an aryl substituent; substituted or not substituted phenyl; substituted or not substituted five or six ring-cycled heteroaryl containing more than one hetero atoms selected from a group consisting of nitrogen, sulfur and oxygen (wherein, phenyl or heteroaryl can be one- or multi-substituted by a substituent selected from a group consisting of hydrogen, methyl, ethyl and isopropyl); $C_1$–$C_3$-alkylcarbonyl; halogeno-$C_1$–$C_3$-alkylcarbonyl; $C_3$–$C_7$-cycloalkylcarbonyl; or $C_1$–$C_5$-alkylcarbonyl containing 1~3 ether bonds (—O—) and/or aryl substituent, and Hal is halogen.

Above all, the process for preparing the compound of formula 1 in the present invention will be illustrated schematically as follows.

<Reaction Formula 1>

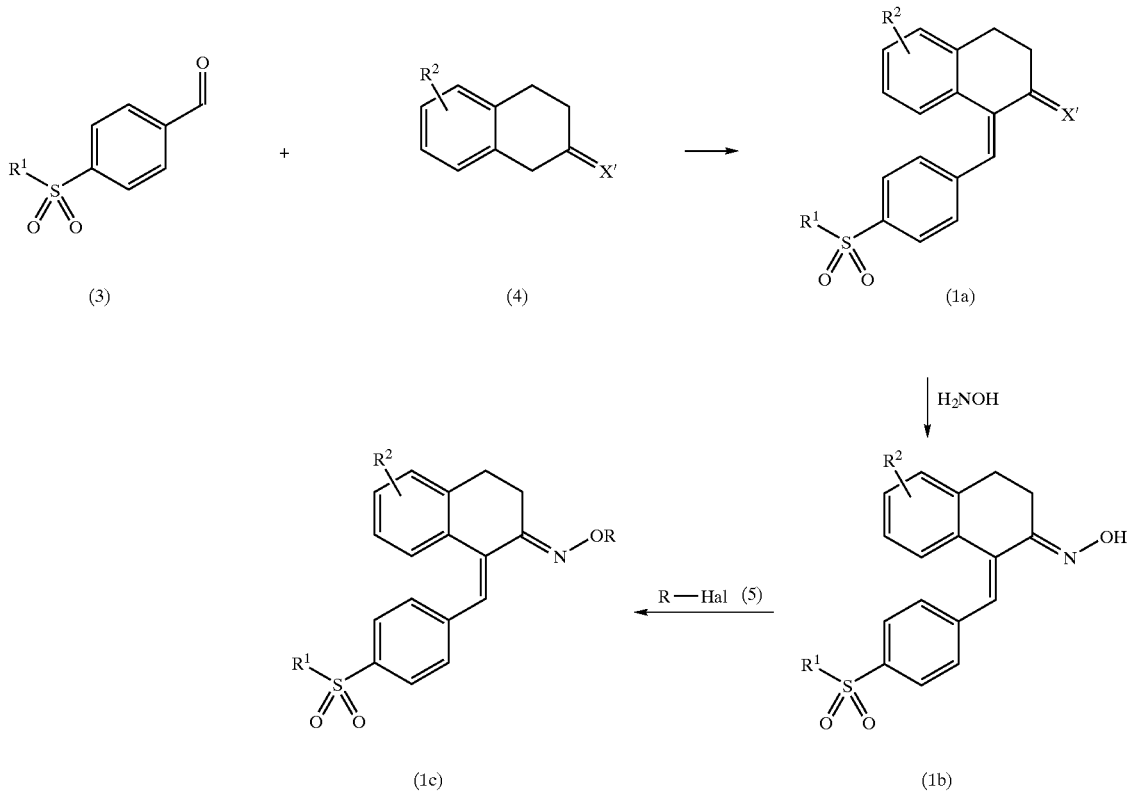

In the reaction formula 1, as initial material a benzaldehyde derivative and a beta-tetralone derivative are reacted, especially under the presence of an acidic catalyst and as a reaction solvent, acetic acid is adopted to produce geometric isomers selectively, namely only (E)-form having a structure of formula 1a. At this moment, the acidic catalyst can be a commonly used inorganic acid and preferably, a halogenized acid such as hydrochloric acid, hydrobromic acid, hydrioic acid and the like. 30% aqueous hydrochloric acid for industrial use is more preferable. The reaction should be accomplished under the presence of acetic acid solvent at a more than freezing point and preferably, under the condition dissolving reactants. Consequently, it should be performed preferably at the range of 0–50° C. and more preferably, at a low temperature in between 5–10° C.

Again, the compound of formula 1a prepared through the procedure explained above is reacted with hydroxylamine so as to produce an oxime compound. At this moment, the hydroxylamine can be a salt form of a conventional hydrochloric acid so as to be utilized conveniently. Therefore, basic substance should be added to neutralize the hydrochloric acid salt and the selection of basic substance can be varied according to a kind of reaction solvent. Preferably, the reaction solvent can be a non-reactive organic solvent utilized commonly in the process of an organic synthesis and namely, selected among dichloromethane, chloroform, tetrahydrofurane, dimethylformamide, benzene, toluene, diethylether and the like. More preferably, dimethylformamide or toluene can be adopted, since the reaction temperature should be relatively higher as demonstrated below. At this moment, the basic substance can be an organic base and preferably, selected among diethylamine, triethylamine, trimethylamine, pyridine, dimethylaminopyridine, piperidine, piperazine and the like, but its kind do not affect the reaction. In addition, it doesn't matter that the reaction is preceded by adding only an organic base and not pouring any organic solvent additionally. Preferably, pyridine is adjusted for this use. The reaction temperature is varied, depending upon a kind of reaction solvent or the composition of added substances. Preferably, it is heated and refluxed at more than room temperatures or at the boiling point of an organic solvent. Lower the reaction temperature becomes, more remarkably the reaction velocity be retarded. Detailed embodiments of the present invention will be illustrated in following Examples. Most preferably, pyridine is heated and refluxed as a sole at the boiling point.

The compound of formula 1b prepared through the above procedure can be substituted at a hydroxyl site of an oxime group by various kinds of functional groups such as aryl, alkyl, acyl and the like. In the present invention, an organic base can be selected from a commonly acceptable group comprising diethylamine, triethylamine, trimethylamine, pyridine, dimethylaminopyridine, piperidine, piperazine and the like and an inorganic base can be selected among sodium acetate, sodium hydroxide, sodium hydride, potassium hydroxide, sodium carbonate, potassium carbonate to perform the reaction. Most preferably, potassium carbonate can be adopted. Under the presence of such a base, a nucleophilic substitution is accomplished with various kinds of halogen compounds such as aryl halide, alkyl halide, acyl halide and the like. Detailed embodiments of the present invention will be illustrated in following Examples.

On the other hand, the process for preparing the compound of formula 2 in the present invention will be illustrated schematically as follows.

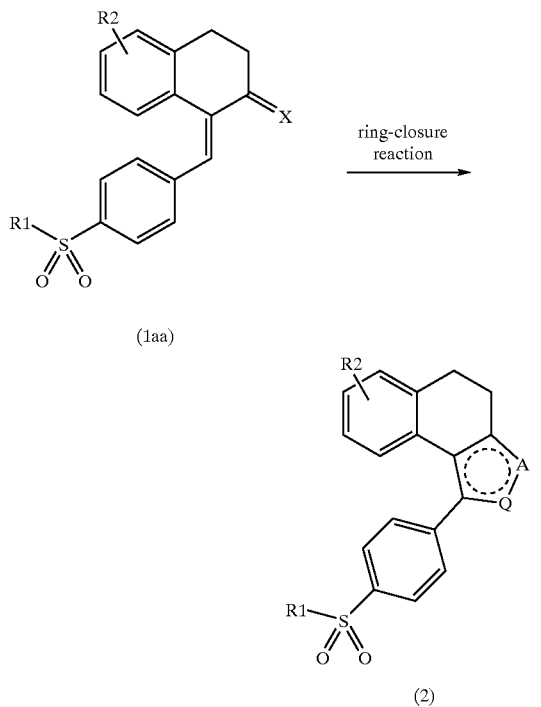

In the reaction formula 2, as initial material alpha-, beta-unsaturated ketone compound is reacted with several reagents containing two hetero atoms such as hydrazine or hydroxylamine substituted or not substituted by $C_1$–$C_3$-alkyl group so that it is possible to produce various kinds of hetero cyclic compounds fused to a 3,4-dihydro-1H-naphthalene structure.

After completing the reaction, the resulting products can be processed through a common treatment such as chromatography, re-crytallization and the like so as to be separated and purified.

The compound of the present invention depicted in formula 1 or formula 2 has an activity for the selective inhibition against cyclooxygenase-2 and thus can be utilized as an enzymatic inhibitor. The compound of formula 1 or formula 2 having a selective inhibitor against cyclooxygenase-2 can be a substitute for conventional non-steroid anti-inflammatory drugs and specially the compound is useful in patients suffering from peptic ulcer, gastritis, partial enteritis, ulcerative colitis, diverticulitis, gastrointestinal haemorrhagia, hypoprothrombinemia and the like as substitute drugs improved in side effects of conventional non-steroid anti-inflammatory drugs. Besides, it is expected to treat inflammatory diseases such as osteoarthritis, rheumatoid arthritis and the like effectively.

The compound of the present invention can be administered in a single dose or in separated doses, depending upon clinical purposes. The specific dosage for patients will vary, depending upon factors such as a sort of drug compound, body weight, sex, physical condition, diet, administration period, administration method, discharge ratio, drug composition and severity of diseases and the like.

The compound of the present invention can be administered as an oral, a local, a parenteral (subcutaneous, venous and muscular silinge or injection), an inhalational or a rectal drug. In case that these are prepared to a pharmaceutical drug, one or more commonly used vehicles, methods for the preparation and the like can be adopted properly from prior arts widely reported to those skilled.

In order to attain the desired purpose of clinical administration, the active compound of formula 1 or formula 2 in the present invention can be administered coincidently by combining more than one components of other commercial drugs.

However, the pharmaceutical drugs containing the compound of the present invention is not limited to forms described above, if it has a purpose for inhibiting cyclooxygenase-2 selectively. All kinds of drugs useful for the enzymatic inhibition can be within the scope of the present invention.

MODES FOR CARRYING OUT THE INVENTION

Practical and presently preferred embodiments of the present invention are illustrative as shown in the following Examples.

However, it will be appreciated that those skilled in the art, on consideration of this disclosure, may make modifications and improvements within the spirit and scope of the present invention.

EXAMPLE 1

Preparation of (E)-1-(4-methanesulfonyl-benzylidene)-3,4-dihydro-1H-naphthalene-2-one 4-methylsulfonylbenzaldehyde (1.0 g, 5.43 mmol) was dissolved in glacial acetic acid (20 ml) and con. Hydrochloric acid (10 ml) was added and cooled at 5–10° C. Then, beta-tetralone (0.72 ml, 5.45 mmol) was dropped slowly and stirred for 3 hours at the same temperature. At room temperature, water (200 ml) and dichloromethane (200 ml) were poured, separated with layers, washed with the saturated brine, dried over anhydrous magnesium sulfate and then concentrated under reduced pressure. The residue was purified by performing a silica gel column chromatography (an eluting agent: ethylacetate/n-hexane=2/3, v/v) and 1.32 g of the present compound (productive yield 78%) was obtained as a yellow crystal.

$^1$H NMR (400 MHz, CDCl$_3$) δ 2.65~2.70 (m, 2H), 3.05 (s, 3H), 3.05~3.10 (m, 2H), 7.00~7.05 (m, 1H), 7.15~7.35 (m, 3H), 7.55 (d, J=8 Hz, 2H), 7.60 (s, 1H), 7.80 (d, J=8 Hz, 2H)

NOESY (400 MHz, CDCl$_3$) 7.15 and 7.55 noe

Mass (FAB) 313.1 (M+1), 625 (2M+1)

melting point: 152~153° C.

EXAMPLE 2

Preparation of (E)-1-(4-methanesulfonyl-benzylidene)-3,4-dihydro-1H-naphthalene-2-one oxime (E)-1-(4-methanesulfonyl-benzylidene)-3,4-dihydro-1H-naphthalene-2-one (50 mg, 0.16 mmol) and hydroxylamine hydrochloride salt (22 mg, 0.32 mmol) was added into pyridine (2.0 ml) and then stirred overnight at reflux condition. Cooled to room temperature, dichloromethane (40 ml) was added, washed twice using 2 N hydrochloric acid (40 ml) and again washed twice using the saturated brine, dried over anhydrous magnesium sulfate, and then concentrated under reduced pressure. The residue was made to solid by adding diisopropylether and n-hexane, filtrated and dried. As a result, 36.7 mg of the present compound (productive yield 70%) was obtained as a white solid.

$^1$H NMR (400 MHz, CDCl$_3$) δ 2.80~2.85 (m, 2H), 2.90~2.95 (m, 2H), 3.10 (s, 3H), 7.00~7.40 (m, 5H), 7.45 (d, J=8 Hz, 2H), 7.80 (d, J=8 Hz, 2H)

Mass (FAB) 328.0 (M+1), 655.1 (2M+1)

melting point: 165~166° C.

EXAMPLE 3

Preparation of (E)-1-(4-methanesulfonyl-benzylidene)-3,4-dihydro-1H-naphthalene-2-one O-ethyl Oxime (E)-1-(4-methanesulfonyl-benzylidene)-3,4-dihydro-1H-naphthalene-2-one oxime (50 mg, 0.15 mmol), ethyl iodide (0.0147 ml, 0.18 mmol) and potassium carbonate (0.063 g, 0.46 mmol) were added into dimethylformamide (2.0 ml). Then, the solution was stirred at 60–65° C. overnight, and cooled to room temperature. Again, water and dichloromethane were added, and an organic layer was separated, washed with water and brine, and dried over anhydrous magnesium sulfate, and then concentrated under reduced pressure to remove organic solvent. The residue was purified through silica gel column chromatography (eluent: ethyl acetate/n-hexane=1/2, v/v). As a result, 44 mg of the present compound (productive yield 81%) was obtained as a white solid crystal.

$^1$H NMR (400 MHz, CDCl$_3$) δ 1.35 (t, J=3 Hz, 3H), 2.75 (t, J=3 Hz, 2H), 2.85 (t, J=3 Hz, 2H), 3.05 (s, 3H), 4.25 (q, J=3 Hz, 2H), 6.95~7.35 (m, 5H), 7.45 (d, J=8 Hz, 2H), 7.75 (d, J=8 Hz, 2H)

melting point: 151–152° C.

EXAMPLE 4

Preparation of (E)-1-(4-methanesulfonyl-benzylidene)-3,4-dihydro-1H-naphthalene-2-one O-methyl Oxime (E)-1-(4-methanesulfonyl-benzylidene)-3,4-dihydro-1H-naphthalene-2-one oxime (50 mg, 0.15 mmol), ethyl iodide (0.023 ml, 0.37 mmol) and potassium carbonate (0.063 g, 0.46 mmol) were added into dimethylformamide (2.0 ml). Then, the solution was stirred at 95~100° C. overnight, and cooled to room temperature. Again, water and dichloromethane were added, and an organic layer was separated, washed with water and brine, and dried over anhydrous magnesium sulfate, and then concentrated under reduced pressure to remove organic solvent. The residue was purified through silica gel column chromatography (eluent: ethyl acetate/n-hexane=1/3, v/v). As a result, 40.7 mg of the present compound (productive yield 78%) was obtained as a white solid crystal.

$^1$H NMR (400 MHz, CDCl$_3$) δ 2.75 (t, J=2 Hz, 2H), 2.85 (t, J=2 Hz, 2H), 3.05 (s, 3H), 4.00 (s, 3H), 6.95~7.25 (m, 5H), 7.45 (d, 2H), 7.75 (d, 2H)

melting point: 175~178° C.

EXAMPLE 5

Preparation of (E)-1-(4-methanesulfonyl-benzylidene)-3,4-dihydro-1H-naphthalene-2-one O-benzyl Oxime (E)-1-(4-methanesulfonyl-benzylidene)-3,4-dihydro-1H-naphthalene-2-one oxime (25 mg, 0.076 mmol), benzyl bromide (0.022 ml, 0.18 mmol) and potassium carbonate (0.032 g, 0.23 mmol) were added into dimethylformamide (1.0 ml). Then, the solution was stirred at 95–100° C. for 48 hours, and cooled to room temperature. Again, water and dichloromethane were added, and an organic layer was separated, washed with water and brine, and dried over anhydrous magnesium sulfate and then concentrated under reduced pressure to remove organic solvent. The residue was purified through silica gel column chromatography (eluent: ethyl acetate/n-hexane=1/3, v/v). As a result, 26 mg of the present compound (productive yield 82%) was obtained as a white solid crystal.

$^1$H NMR (400 MHz, CDCl$_3$) δ 2.75~2.85 (m, 4H), 3.05 (s, 3H), 5.25 (s, 2H), 6.95~7.40 (m, 10H), 7.45 (d, J=8 Hz, 2H), 7.75 (d, J=8 Hz, 2H)

EXAMPLE 6

Preparation of 1-(4-methanesulfonyl-phenyl)-4,5-dihydro-2H-benzo[e]indazole (E)-1-(4-methanesulfonyl-benzylidene)-3,4-dihydro-1H-naphthalene-2-one (50 mg, 0.16 mmol), hydrazine hydrate (0.0155 ml, 0.32 mmol) were added into ethanol (5.0 ml) and 1–2 drops of acetic acid was added properly. Then, the solution was stirred and refluxed for 48 hours and cooled to room temperature. Afterward, the resulting solution was concentrated under reduced pressure, diluted by adding dichloromethane (10 ml), and then washed with water and the saturated brine. The residue was purified through silica gel column chromatography (eluent: ethylacetate/n-hexane=1/1, v/v). As a result, 35 mg of the present compound (productive yield 68%) was obtained as a brown solid.

$^1$H NMR (400 MHz, CDCl$_3$) δ 3.00 (t, J=8 Hz, 2H), 3.20 (t, J=8 Hz, 2H), 3.25 (s, 3H), 7.15~7.45 (m, 4H), 7.95 (d, J=7 Hz, 2H), 8.20 (d, J=7 Hz, 2H)

Mass (FAB) 325.1 (M+1), 649.1 (2M+1)

melting point: 178~180° C.

EXAMPLE 7

Preparation of 1-(4-methanesulfonyl-phenyl)-4,5-dihydro-naphto[2,1-c]isooxazole (E)-1-(4-methanesulfonyl-benzylidene)-3,4-dihydro-1H-naphthalene-2-one (50 mg, 0.16 mmol) were dissolved in ethanol (2.0 ml) and then anhydrous sodium acetate solution (14.5 mg, 0.18 mmol, saturated with hot acetic acid) and hydroxylamine hydrochloride salt solution (12.2 mg, 0.18 mmole, ethanol 2.0 ml) were added respectively. Then, the solution was heated and refluxed for about 5 hours and cooled to room temperature. Afterward, water and dichloromethane were added, separated to layers, washed with the saturated brine and then dried over anhydrous magnesium sulfate. The resulting solution was concentrated under reduced pressure so as to obtain a solid. Again, toluene (5 ml) was poured, refluxed, stirred for 24 hours and cooled to room temperature. After condensing with reduced pressure, the resulting remnant was purified through silica gel column chromatography (eluent: ethyl acetate/n-hexane=1/1, v/v).

As a result, 35 mg of the present compound (productive yield 71%) was obtained.

$^1$H NMR (400 MHz, CDCl$_3$) δ 2.95~3.10 (m, 4H), 3.15 (s, 3H), 7.15~7.50 (m, 4H), 8.00~8.10 (m, 4H)

Mass (FAB) 326.1 (M+1)

melting point: 181~182° C.

EXAMPLE 8

Preparation of (E)-1-(4-methanesulfonyl-benzylidene)-3,4-dihydro-1H-naphthalene-2-one O-acetyl-oxime (E)-1-(4-methanesulfonyl-benzylidene)-3,4-dihydro-1H-naphthalene-2-one oxime (25 mg, 0.076 mmol) and acetylbromide (0.017 ml, 0.23 mmol) were added into dichloromethane (2.0 ml). Then, at room temperature triethylamine (0.032 ml, 0.23 mmol) was added, stirred for an hour so as to complete the reaction. Afterward, an organic layer was separated by blending water, washed again with water and saturated brine, and then dried over anhydrous magnesium sulfate. The resulting solution was concentrated under reduced pressure and made to crystal by using a mixed organic solvent (diethylether/isopropanol/n-hexane=1/1/5, v/v/v). As a result, 16.9 mg of the present compound (productive yield 60%) was obtained as a white solid crystal.

$^1$H NMR (400 MHz, CDCl$_3$) δ 2.25 (s, 3H), 2.85~2.95 (m, 4H), 3.05 (s, 3H), 7.00~7.10 (m, 2H), 7.25~7.30 (m, 2H), 7.40 (s, 1H), 7.45 (d, J=4 Hz, 2H), 7.75 (d, J=6.4 Hz, 2H)

Mass (FAB) 370.1 (M+1)

melting point: 70~73° C.

EXAMPLE 9

Preparation of (E)-1-(4-methanesulfonyl-benzylidene)-3,4-dihydro-1H-naphthalene-2-one O-benzyloxyacetyl-oxime (E)-1-(4-methanesulfonyl-benzylidene)-3,4-dihydro-1H-naphthalene-2-one oxime (50 mg, 0.15 mmol) and benzyloxyacetylchloride (0.029 ml, 0.18 mmol) were added into dichloromethane (5.0 ml). Then, at 0~5° C. triethylamine (0.026 ml, 0.18 mmol) was added, stirred for 15 minutes so as to complete the reaction. Afterward, an organic layer was separated by blending water, washed again with water and saturated brine and then dried over anhydrous magnesium sulfate. The resulting solution was concentrated under reduced pressure and made to crystal by using diisopropylether. As a result, 40.7 mg of the present compound (productive yield 56%) was obtained as a white solid crystal.

$^1$H NMR (400 MHz, CDCl$_3$) δ 2.80~2.90 (m, 4H), 3.05 (s, 3H), 4.30 (s, 2H), 4.70 (s, 2H), 7.00~7.05 (m, 1H), 7.10 (s, 1H), 7.25~7.40 (m, 9H), 7.45 (d, J=8 Hz, 2H), 7.80 (d, J=8 Hz, 2H)

$^{13}$C NMR (100 MHz, CDCl$_3$), δ 23.3, 25.8, 27.3, 44.8, 44.9, 66.9, 73.9, 127.2, 127.8, 128.3, 128.4, 128.5, 128.9, 129.0, 129.1, 129.5, 130.3, 132.5, 133.8, 137.4, 139.0, 139.9, 142.0, 167.5, 168.6

Mass (FAB) 476.1 (M+1)

EXAMPLE 10

Preparation of 1-(4-methanesulfonyl-phenyl)-2-methyl-4,5-dihydro-2H-benzo[e]imidazole (E)-1-(4-methanesulfonyl-benzylidene)-3,4-dihydro-1H-naphthalene-2-one (50 mg, 0.16 mmol) and methylhydrazine (0.042 ml, 0.79 mmol) were added into pyridine (2.0 ml), refluxed and stirred for 12 hours. After cooled at room temperature, 5.0 ml of water was added, diluted and then, conc. hydrochloric acid was dropped properly. Then, the reacted solution was neutralized, extracted with dichloromethane (10 ml) and washed with water and saturated brine. The resulting solution was concentrated to be purified through silica gel column chromatography (eluent: ethyl acetate/n-hexane=4/1, v/v). As a result, 30 mg of the present compound (productive yield 55%) was obtained as a brown solid.

$^1$H NMR (400 MHz, CDCl$_3$) δ 2.80~2.95 (m, 4H), 3.15 (s, 3H), 3.85 (s, 3H), 6.95~7.15 (m, 4H) 7.70 (d, J=8 Hz, 2H), 8.10 (d, J=8 Hz, 2H)

Mass (FAB) 339.1 (M+1)

EXPERIMENTAL EXAMPLE

The Activity of Selective Inhibition against cyclooxygenase-2

(1) Experimental Procedure

In order to investigate the activity of the present compound for the selective inhibition against cyclooxygenase-2 enzyme pharmacologically, the enzymatic activities inhibiting cyclooxygenase-1 and cyclooxygenase-2 were measured quantitatively.

First of all, the cyclooxygenase-1 was examined through the following procedure.

Peritoneal fluid in which macrophages were suspended was extracted from a mouse peritoneal cavity and centrifuged at 4° C., 1,000 rpm for 2 minutes. Then, the supernatant was removed, suspended with 20 ml of incomplete (no serum) RPMI medium [PC/SM (penicilin/streptomycin)] and again centrifuged under the same condition. In addition, the reactant was washed twice and then the cell pellet was suspended with 10 ml of incomplete RPMI 1640 medium so as to prepare a cell suspension. Then, the cell number was calculated with the hemocytometer and adjusted to reach 1×10$^6$ cells/ml of cell concentration in the final cell suspension. 100 μl of the resulting suspension was transferred into each well of 96-well plate and left at 37° C. in 5% CO$_2$ with the incubator for about 2 hours in order to attach macrophages. The attached macrophage was washed twice by using PBS buffer, treated to experimental samples in a proper concentration and then blended with 3% FBS-RPMI 1640 medium so as to adjust the total volume reaching 200 μl. The resulting cell was cultivated in the incubator at 37° C. in 5% CO$_2$ for about 12~16 hours. Then, arachidonic acid was added, adjusting to 10 μM of a final concentration and incubated at 37° C. for more 10 minutes and the supernatant of the reacted solution (~180 μl) was recovered to finish the reaction. In order to quantitate the amount of PGE2 in the samples, the ELISA method recommended from Cayman Chemical company was exploited and the obtained results was used to estimate the inhibition ratio (%) of each compound against cyclooxygenase-1.

Second, the cyclooxygenase-2 was examined through the following procedure.

Peritoneal fluid suspended with macrophages was extracted from a mouse peritoneal cavity and centrifuged at 4° C., 1,000 rpm for 2 minutes. Then, the supernatant was removed, suspended using incomplete RPMI medium [PC/SM (penicilin/streptomycin)] and again centrifuged under the same condition. In addition, the reactant was washed twice and then the cell pellet was suspended with 10 ml of incomplete RPMI 1640 medium so as to prepare a cell suspension. Then, the cell number was calculated with the hemocytometer and adjusted to reach $1\times10^6$ cells/ml of cell concentration in the final cell suspension. The resulting suspension was treated with aspirin, adjusting 500 µM of final concentration and transferred into each well of 96-well plate in 100 µl respectively. Again, it was left at 37° C. in 5% $CO_2$ in the incubator for about 2 hours in order to attach macrophages. The attached macrophage was washed twice by using PBS buffer, treated to experimental samples in a proper concentration and then blended with 3% FBS-RPMI 1640 medium containing 10 µg/ml of LPS in each well. The resulting cell was cultivated in the incubator at 37° C. in 5% $CO_2$ for about 12~16 hours. Then, arachidonic acid was added, adjusting to 10 µM of a final concentration and incubated at 37° C. for more 10 minutes and the supernatant of the reacted solution (~180 µl) was recovered to finish the reaction. In order to quantitate the amount of PGE2 in the samples, the ELISA method recommended from Cayman Chemical company was exploited and the obtained results was used to estimate the inhibition ratio (%) of each compound against cyclooxygenase-2.

(2) Experimental Results

The experimental results were demonstrated in Table 1 as follows.

TABLE 1

Inhibitory effects of cyclooxygenase (COX) (unit: % inhibition)

| | Examples | | | | | |
|---|---|---|---|---|---|---|
| | COX-1 | | | COX-2 | | |
| Concentration | 30 µM | 10 µM | 3 µM | 300 nM | 100 nM | 30 nM |
| SC-58635 (standard substance) | 81.3 | 66.5 | 64.3 | 73 | 59.9 | 51.2 |
| 1 | 45.8 | 40.7 | 33.2 | ~0 | ~0 | ~0 |
| 2 | 80.4 | 68.7 | 56.7 | 22 | 20.7 | 15.7 |
| 3 | 74.6 | 64.4 | 60.4 | 70.2 | 58.8 | 50.1 |
| 4 | 80.1 | 71.1 | 60.3 | 81.5 | 69.9 | 55.4 |
| 5 | 54.3 | 47.1 | 39.9 | 61.4 | 55.4 | 51.2 |
| 6 | 64.8 | 57.3 | 52.3 | 54.9 | 46.6 | 33.4 |
| 7 | 56.4 | 44.1 | 30 | 76.8 | 70.6 | 59.8 |
| 8 | 53.9 | 32.3 | 7.6 | 29.6 | 28.6 | 22.1 |
| 9 | 42.1 | 31.1 | 22.8 | 30.1 | 25.5 | 20.4 |
| 10 | 61.5 | 55.3 | 49.8 | 61.0 | 31.8 | 20.2 |

In vitro experiments were observed to measure the inhibitional ratios against cyclooxygenase-1 (COX-1) and cyclooxygenase-2 (COX-2). Consequently, in case of the compound of Example 7, 1-(4-methansulfonyl-phenyl)-4,5-dihydro-naphtho[2,1-c]isooxazole, the inhibition effect against cyclooxygenase-2 was identified to be more excellent than a comparative substance and coincidently, the inhibition effect against cyclooxygenase-1 be in much lower level than a comparative substance. That is to say, the selectivity of cyclooxygenase-2 is confirmed to be better than any other substances, which proves the structural efficacy of 1H-indole derivatives in the present invention.

INDUSTRIAL APPLICABILITY

As demonstrated and confirmed above, the novel compound of 3,4-dihydro-1H-naphthalene derivative is a substitute drug improved in side effects of conventional non-steroid anti-inflammatory drug and is useful for patients suffering from peptic ulcer, gastritis, partial enteritis, ulcerative colitis, diverticulitis, gastrointestinal haemorrhagia, hypoprothrombinemia and the like. Besides, it is expected to treat inflammatory diseases such as osteoarthritis, rheumatoid arthritis and the like effectively.

Those skilled in the art will appreciate that the conceptions and specific embodiments disclosed in the foregoing description may be readily utilized as a basis for modifying or designing other embodiments for carrying out the same purposes of the present invention.

Those skilled in the art will also appreciate that such equivalent embodiments do not depart from the spirit and scope of the invention as set forth in the appended claims.

What is claimed is:

1. A compound of formula 1, its pharmaceutically acceptable salts and its geometric isomers

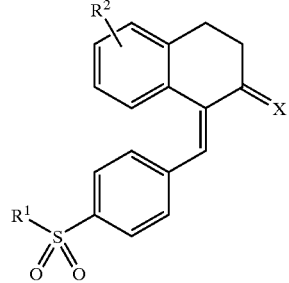

<Formula 1> wherein $R^1$ is selected from a methyl or amino group, $R^2$ is selected from the group consisting of hydrogen, halogen C1–C3-alkyl substituted or not substituted by halogens, amino, hydroxy, hydroxycarbonyl, nitro or cyano group, and X is an oxime as a substituted or not substituted form.

2. The compound of formula 1 according to claim 1, in which $R^1$ is methyl group, $R^2$ is hydrogen and X is an oxime (=N—OH) as a substituted or not substituted form wherein a substituent for said oxime is selected from the group consisting of methyl, ethyl, benzyl, acetyl or benzyloxyacetyl group.

3. The compound according to claim 1, wherein said compound of formula 1 is selected from the group consisting of:

(E)-1-(4-methanesulfonyl-benzylidene)-3,4-dihydro-1H-naphthalene-2-one oxime;

(E)-1-(4-methanesulfonyl-benzylidene)-3,4-dihydro-1H-naphthalene-2-one O-ethyl-oxime;

(E)-1-(4-methanesulfonyl-benzylidene)-3,4-dihydro-1H-naphthalene-2-one O-methyl-oxime;

(E)-1-(4-methanesulfonyl-benzylidene)-3,4-dihydro-1H-naphthalene-2-one O-benzyl-oxime;

(E)-1-(4-methanesulfonyl-benzylidene)-3,4-dihydro-1H-naphthalene-2-one O-acetyl-oxime; and (E)-1-(4-methanesulfonyl-benzylidene)-3,4-dihydro-1H-naphthalene-2-one O-(benzyloxyacetyl)-oxime.

4. The compound according to claim 1, wherein said halogen is selected from the group consisting of fluoride, chloride, bromide and iodide.

* * * * *